United States Patent [19]

Stoddard

[11] Patent Number: 6,014,585
[45] Date of Patent: Jan. 11, 2000

[54] METHOD OF TREATING PAIN USING ION CONDUCTING TAPE

[76] Inventor: Darrell J. Stoddard, 266 E. 3200 North, Provo, Utah 84604

[21] Appl. No.: 08/899,351

[22] Filed: Jul. 23, 1997

[51] Int. Cl.[7] .................................................. A61N 1/00
[52] U.S. Cl. .................................. 607/2; 607/46; 128/898
[58] Field of Search .............................. 607/1, 2, 46, 115, 607/152, 153; 128/898

[56] References Cited

U.S. PATENT DOCUMENTS

| | | | |
|---|---|---|---|
| 526,182 | 9/1894 | Fritsche | 607/115 |
| 683,098 | 9/1901 | Baecker | 607/115 |
| 4,243,051 | 1/1981 | Wittemann | 607/152 |
| 4,398,545 | 8/1983 | Wilson | 607/46 |
| 4,619,252 | 10/1986 | Ibbott | 607/1 |
| 4,653,473 | 3/1987 | Kempe . | |
| 4,825,877 | 5/1989 | Kempe . | |
| 5,374,283 | 12/1994 | Flick | 607/46 |
| 5,423,874 | 6/1995 | D'Alerta | 607/72 |

FOREIGN PATENT DOCUMENTS

| | | | |
|---|---|---|---|
| 3222967 | 10/1991 | Japan | 607/1 |
| 9-299395 | 11/1997 | Japan . | |
| 0002981 | of 1892 | United Kingdom | 607/1 |
| 0182650 | 7/1922 | United Kingdom | 607/1 |

*Primary Examiner*—Jeffrey R. Jastrzab
*Attorney, Agent, or Firm*—Delbert R. Phillips

[57] ABSTRACT

Pain is relieved by application of a electrical/ion conductive tape over the pain site. This tape promotes the flow of minute endogenous electrical currents. The use of the tape in most cases immediately relieves the pain.

11 Claims, 1 Drawing Sheet

METHOD OF TREATING PAIN USING ION CONDUCTING TAPE

BACKGROUND OF THE INVENTION

Doctors have been trying for more than 200 years to find out what causes pain without ever learning what pain is. Injury causes pain but what is the cause of pain when there has been no injury? Pain may continue long after an injury takes place. Why does it still hurt? What is pain? How does the body heal pain? Every cell is a tiny chemical/electric generator connected electrically to other cells. The sensation of touch occurs when cells are pushed closer together. This decreases the electrical resistance between cells. Decreasing the electrical resistance increases the flow of electricity to the brain. The increased flow of electricity is interpreted as touch.

A hit to the body sends a quick burst of electricity to the brain. This quick burst is interpreted by the brain as pain. If pain continues after the blow, it is because tissue has been damaged and electrical connections between cells have been broken. The brain senses the injury because of a signal from the damaged tissue to the brain. A pain signal, however, is not the pain! Pain is broken or suppressed electrical connections between cells in the injured tissue. Degenerative diseases, dehydration, infection, ulcers, tumors, spontaneous fractures, allergies, lack of minerals, etc. may also cause the electrical circuits to fail, even without injury. Whether it is the breaking of the electrical circuits from an injury or the failure of electrical signals for other reasons, the signal to the brain is the same. They are all interpreted as pain.

Pain is healed when the body reconnects the broken circuits. Suppressing the pain signal with medication is treating the symptom, not the cause. The medication does nothing for the broken circuits that cause the pain.

A part of the body that hurts always has more electrical resistance. The electrical connections between cells are suppressed. The restoration of the flow of electricity through the painful area will relieve the pain often immediately.

Several approaches to the control of pain are known. The Chinese use acupuncture that entails placing needles on specific areas of the body. Traditional medicine uses palliative therapies such as heat and cold, analgesics, narcotics, and surgery to combat pain. Pain medications only mask symptoms, suppress vital functions, or cause gastrointestinal bleeding. Hypnotism and other psychological methods are also employed in pain treatment.

The device shown in U.S. Pat. No. 5,374,283 to Flick issued Dec. 20, 1994 is illustrative of the use of the external application of the electrical current to treat pain. The patent has an electrical pulse producing device coupled to a nylon wrap coated with silver which acts as a conductor for external current. A second electrode is placed on the skin and the current passes between the wrap and the second electrode. The method described in the Flick patent requires the use of external electric current. The use of external electrical current is not contemplated by the instantly claimed method.

U.S. Pat. No. 5,423,874 to D'Alerta issued Jun. 13, 1995 is drawn to an electronic patch device for preventing nerves from transmitting "pain" information to the brain. It is composed of a circuit layer that supports an electronic circuit, a double sided adhesive layer, a top layer that seals the circuit layer from moisture and a backing layer. A cathode and an anode are disposed in apertures of the adhesive layer and make electrical contact with respective pins of the electronic circuit in the circuit layer. On opposite surfaces the cathode and anode are exposed to make contact with the skin of a patient when the backing layer is removed. Again this device depends on external currents for pain suppression.

U.S. Pat. No. 683,098 to L. Baecker issued Sep. 24, 1901 is drawn to a cloth with zinc and copper interwoven. The zinc and copper produce electrical current when warmed by the temperature of the body. The patent does not suggest that the cloth will treat pain.

U.S. Pat. No. 526,182 to F. Fritsche issued on Sep. 18, 1894 is drawn to a galvanic chain composed of two separate chains one being copper and the other being zinc, which is designed to be worn around the neck. The chains are connected by threads of wool. When the wool absorbs moisture from the body, it purportedly acts as an electrolyte between the two metals by that causing a current to flow. This current flow is claimed as a remedy for various ailments including pain. Obviously this patent does not suggest the instantly claimed method of treating pain.

U.S. Pat. No. 4,825,877 to Kempe issued May 2, 1989. This patent is drawn to an application of cloth containing stainless steel fibers to painful muscles. The patent teaches that the relief is obtained by shielding the painful muscles from radiation.

U.S. Pat. No. 4,653,473 to Kempe issued Mar. 31, 1987. This patent is drawn to the application of a cloth containing stainless steel fibers to stumps of amputees to shield the stumps from radiation and therefore preventing phantom pain.

The Kemper patents do not use or suggest a flexible electrically conductive tape which adheres to the skin for the treatment of pain.

SUMMARY OF THE INVENTION

By measuring electrical potentials across the site of pain in the human body, it has been discovered that pain is caused by the breaking, cutting or shutting off the minute electrical current or potentials that pass through the cells in the body. When electrical conductivity is restored across the painful area, the pain is relieved. This conductivity can be restored by application of an appropriate length of ion/electrical conductive pressure sensitive tape across the pain site. When the tape is applied across the pain site, the pain was relieved almost immediately.

Figure 1:
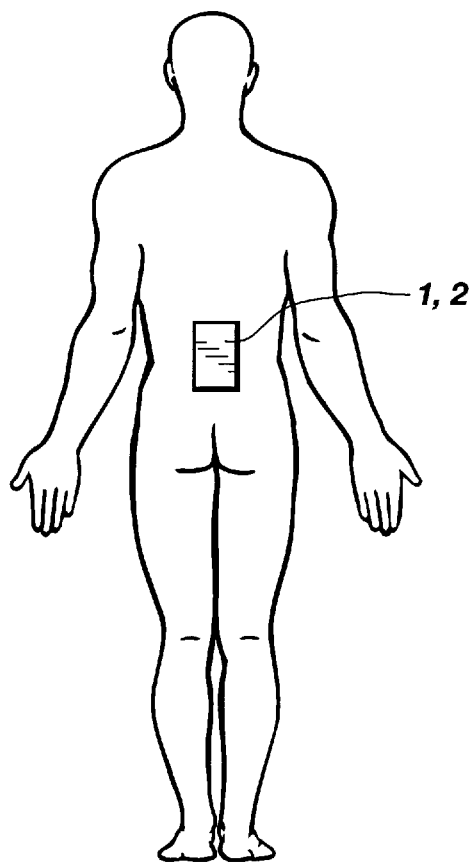
FIG. 1 shows the conductive tape applied across the area of back pain.
Figure 2:
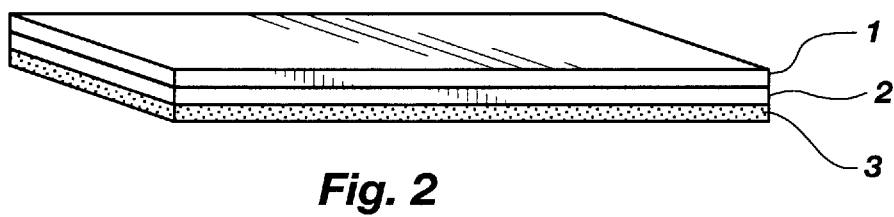
FIG. 2 shows the construction of the three layer tape.
Figure 3:
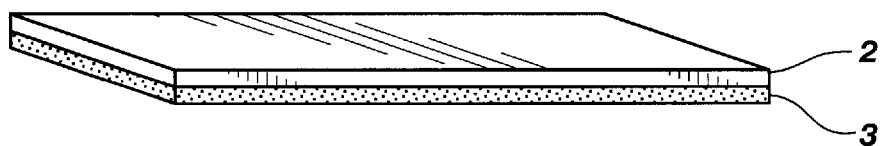
FIG. 3 shows the construction of the two layer tape.

The electrical conductive tape comprises a hypoallergenic adhesive layer 3 capable of conducting minute electrical currents and a second layer of flexible conductive material. The flexible conductive material 2 is selected from the group consisting of electrically conductive plastic material and flexible sheet material coated or plated with an electrically conductive metal such as copper, silver, or gold. The sheet material may be fabric, plastic or any other flexible material that can be plated or coated with metal. The tape may have a third layer of protective material 1 that resists tearing and provides additional strength. This third layer may be rip-stop nylon or other material that resists abrasion and tearing. The adhesive layer must be in direct contact with the conductive material in the second layer.

The tape is applied across the area of pain and firmly pressed onto the skin allowing the endogenous electric current, to flow through the conductive layer thus bypassing the injured area, restoring the endogenous ion/electrical flow and thereby relieving the pain. This method of receiving pain is non invasive. No medicaments are used. The tape is chemically inert. No external electrical currents are used. The sole purpose of the tape is to conduct electrical potentials produced by cells in the body facilitating the natural flow of endogenous minute electrical currents over the pain site past the interruption of endogenous current thus relieving pain.

EXAMPLES

The following examples used ARclad® 8010, a tape manufactured by Adhesives Research, Inc. This tape is a single coated conductive plastic film featuring homogeneously conductive EC-3 conduct adhesive. The product has a protective 60 lb. kraft release liner on one side. The product has the following electrical properties: volume Resistance (ohms/inch$^2$) 10, Surface Resistance (ohms/cm$^2$) 80, and Static Dissipation FAST (Arcing). The conductive layer has conductive carbon incorporated therein.

In the following case studies this tape is referred to as carbon tape:

Ben C. was diagnosed with Osgood Slaughters Disease and experienced immediate pain relief after carbon tape was applied to the knee.

Heidi B. suffered from sciatica pain in low back and down buttocks and legs to feet. Carbon tape was applied on the pain site which relieved 95% of the pain within minutes. This pain has not returned.

Anne C. had pain in her heel and Achilles tendon for six months prior to treatment. Application of the carbon tape completely relieved the pain with only one application.

Marvin W. suffered for five years with severe pain in the balls of his feet making them almost too tender to walk on for five years. Carbon tape was applied to the pain area and pain was eliminated until the tape came off.

Joleen S. suffered Thoracic outlet pain so severe that she could not lay down to sleep for six months. Carbon tape was applied to the area of pain and complete relief was reported.

Judi S. had a painful knee and shoulder. Application of Carbon tape to the pain site relieved the pain. Four months later the pain is still 80% relieved.

Helen S. is a ninety-year-old women with pain that continued for three years after knee joint replacement surgery. The pain was so severe that she could not walk. Carbon tape was applied to her knee and within 15 minutes she was walking and 90–100% of the pain was gone. After the tape was removed a month later, the pain was completely gone.

Mary E. had sciatic pain. Carbon tape was applied over the pain area and she was able to bend over for the first time in 10 years without pain. A month after the treatment a 90% reduction of her pain was still experienced.

Paul S. had back pain so severe he could not attain an upright position. Carbon tape was applied over the pain site. Pain was completely gone the following morning and has not returned for three months.

The following examples used the tape manufactured by 3M advertised as product number 1181 composed of a combination of copper-plated smooth ripstop polyester fabric backing and a conductive adhesive. In the following cases this product is referred to as copper tape.

Dorothy S. suffered from arthritis in knees with pain and swelling sufficient to prevent walking. Copper tape applied around both knees relieved almost 100% of the pain immediately and swelling was eliminated in two days without recurrence. The above treatment was repeated for pain without swelling on Oct. 29, 1996, Nov. 25, 1996, Dec. 10, 1996, Jan. 7, 1997, Feb. 11, 1997. Total relief of pain each time was experienced. Carbon tape was applied Mar. 5, 1997, Apr. 17, 1997, and Jun. 25, 1997. She received total relief of pain each time that lasted a month or more.

Royola A. had severe low back pain from a injury sustained while jumping on a trampoline. Copper tape was applied to the right side of her lumbar spine Nov. 11, 1996. There was 95% relief of pain within seconds and after reapplication of the copper tape Jan. 6, 1997, pain was still 75% improved. No more treatments were necessary after Jul. 11, 1997.

Hope P's arm and shoulder ached like a toothache all night possibly from lymph edema after mastectomy. Copper tape was applied over her shoulder and down to her hand on Oct. 7, 1996. One hundred percent relief was experienced by the next night and the pain has not returned as of Jul. 11, 1997.

Jeff R. experienced low back pain. Copper tape was applied over the pain area. Pain was relieved immediately. Patient replaced tape two times when pain returned with total relief experienced each time.

Terry G. had pain so severe in low back that he couldn't walk. Copper tape was applied Feb. 11, 1997. There was almost immediate "miraculous" relief after application of the tape. Tape was reapplied May 2, 1997 when pain started to return. Pain was relieved again and had not returned two months later.

Colleen M. had rheumatoid arthritis pain in her hands. Three strips of copper tape were applied down her arm to her hand Oct. 8, 1996. She received 90% relief within minutes.

Bret A. had a groin pull. Copper tape was applied and the pain significantly diminished within an hour.

Eda A. had copper tape applied over painfil cord on the side of her neck and she experienced 80% relief of pain immediately.

Lisa S. had low back pain during pregnancy. Copper tape was applied down both sides of lumbar spine and gave 95% pain relief.

Jane R. had a very painful "frozen shoulder". Copper tape applied to the shoulder gave nearly 100% relief immediately.

Lois C. had excruciating endless pain resulting from knee surgery in 1987. Copper tape was applied Dec. 12, 1996. Patient reported Jul. 12, 1997 that the relief of pain from one application of the tape is "the greatest joy in my entire life." The patient has been pain free for eight months after suffering for nine years.

Mary Jo. was severely disabled as a result of polio. Copper tape was applied over swollen knee Jan. 3, 1997. Patient reported Jan. 13, 1997 that the tape helped, tremendously. She was able to walk through the grocery store for the first time in years and "was not crippled after doing it."

Summer D. suffered from continuous lumbar pain from a cheer leading accident two years earlier. Copper tape was applied Sep. 18, 1996 to the left of her lumbar spine. Pain was eliminated until Oct. 23, 1996. The copper tape was reapplied Oct. 24, 1996. Pain has still not returned as of Jul. 13, 1997.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for controlling pain by facilitating the flow of endogenous electrical currents in the body consisting of, without the application of external electrical currents, applying adhesive electrical conductive tape on the body over a pain site.

2. A method of claim 1 which further comprises, applying over said pain site said electrical conductive tape which further comprises an adhesive layer having the ability to conduct minute electrical currents and a second layer of electrically conductive material;

said adhesive layer being in direct contact with said second layer of electrically conductive material.

3. A method as claimed in claim 2 comprising, applying over said pain site said electrical conductive tape which further comprises a protective layer of material bonded to said second layer.

4. A method as claimed in claim 3 further comprising applying over said pain site said electrical conductive tape wherein said electrical conductor is metal plated fabric.

5. A method as claimed in claim 4 further comprising applying over said pain site said electrical conductive tape, wherein said metal in said metal plated plastic fabric is selected from the group consisting of silver, copper and gold.

6. A method as claimed in claim 5 further comprising applying over said pain site said electrical conductive tape wherein said metal is copper.

7. A method as claimed in claim 6 comprising applying over said pain site said electrical conductive tape wherein said electrical conductor is a conductive plastic.

8. A method as claimed in claim 2 which further comprises applying over the pain site said electrical conductive tape wherein said conducting material further comprises a flexible material combined with an electrical conductor.

9. A method for controlling pain by facilitating the flow of endogenous minute electrical currents over the pain site comprising, without the application of external electrical currents, applying an electrical conductive tape further comprising three layers, a rip stop outer layer, a layer of electrically conducting carbon and a layer of electrical conductive adhesive.

10. A method for controlling pain by facilitating the flow of endogenous minute electrical currents over the pain site comprising applying on the skin over the pain site an electrical conductive tape, without the application of external electrical currents, further comprising a combination of copper-plated ripstop polyester fabric backing and a conductive adhesive.

11. A method for controlling pain by facilitating the flow of endogenous electrical currents in the body comprising, without the application of external electrical currents, applying adhesive electrical conductive tape on the body over a pain site;

said electrical conductive tape further comprising an adhesive layer having the ability to conduct minute electrical currents and a second layer of electrically conductive material;

said adhesive layer being in direct contact with said second layer of electrically conductive material;

said conductive material further comprises a flexible material combined with an electrical conductor;

said electrical conductor is a conductive plastic;

said conductive plastic contains electrically conductive carbon.

* * * * *